(12) United States Patent
Rosen

(10) Patent No.: US 7,964,212 B2
(45) Date of Patent: *Jun. 21, 2011

(54) EFFERVESCENT COMPOSITIONS COMPRISING PHOSPHONATES AND METHODS RELATED THERETO

(76) Inventor: Christer Rosen, Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/367,928

(22) Filed: Feb. 9, 2009

(65) Prior Publication Data

US 2009/0142278 A1 Jun. 4, 2009

Related U.S. Application Data

(63) Continuation of application No. 10/273,081, filed on Oct. 17, 2002, now Pat. No. 7,488,496, which is a continuation-in-part of application No. 10/092,083, filed on Mar. 6, 2002, now abandoned.

(51) Int. Cl.
*A61L 15/16* (2006.01)
*A61K 31/66* (2006.01)

(52) U.S. Cl. ........................................ 424/446; 514/114

(58) Field of Classification Search .................. 514/114; 424/446

See application file for complete search history.

(56) References Cited

U.S. PATENT DOCUMENTS

| | | | |
|---|---|---|---|
| 4,393,531 A | 7/1983 | Gergely et al. | |
| 4,462,982 A | 7/1984 | Samejima et al. | |
| 4,621,077 A | 11/1986 | Rosini et al. | |
| 4,687,662 A | 8/1987 | Schobel | |
| 4,710,384 A | 12/1987 | Rotman | |
| 4,942,039 A | 7/1990 | Duvall et al. | |
| 5,178,878 A | 1/1993 | Wehling et al. | |
| 5,270,365 A | 12/1993 | Gertz et al. | |
| 5,348,745 A | 9/1994 | Daher | |
| 5,393,531 A | 2/1995 | Gerhard et al. | |
| 5,415,870 A | 5/1995 | Gergely et al. | |
| 5,480,652 A | 1/1996 | Bru-Magntez et al. | |
| 5,488,041 A | 1/1996 | Barbier et al. | |
| 5,646,134 A | 7/1997 | Yates | |
| 5,709,886 A | 1/1998 | Bettman et al. | |
| 5,853,759 A | 12/1998 | Katdare et al. | |
| 5,994,329 A | 11/1999 | Daifotis et al. | |
| 6,015,801 A | 1/2000 | Daifotis et al. | |
| 6,225,294 B1 | 5/2001 | Daifotis et al. | |
| 6,284,272 B1 | 9/2001 | Chiesi et al. | |
| 6,333,316 B1 | 12/2001 | Daifotis et al. | |
| 2001/0002395 A1 | 5/2001 | Daifotis | |

FOREIGN PATENT DOCUMENTS

| | | |
|---|---|---|
| EP | 1127573 | 8/2001 |
| GB | 2153225 | 8/1985 |
| WO | WO 9311774 | 6/1993 |
| WO | WO 9414455 | 7/1994 |
| WO | WO 9641618 | 12/1996 |
| WO | WO 97/44017 | 11/1997 |
| WO | WO 9744017 | 11/1997 |
| WO | WO 01/39724 | 6/2001 |
| WO | WO 139724 | 6/2001 |
| WO | WO 01/52848 | 7/2001 |

OTHER PUBLICATIONS

Bull, An Introduction to Physical Biochemistry, 1964, p. 103.
Goodman et al., The Pharmacological Basis to Therapeutics, Ninth Edition, 1995, p. 51.
Gertz at at, Studies of the Oral Bioavailability of Alendronate, Clinical Pharmacology & Therapeutics, Sep. 1995, pp. 285-298.
2000, Aldrich Handbook of Fine Chemicals and Laboratory Equipment, pp. 436, 1498, and 1505.
Dobrucali et al., Physiological and Morphological Effects of Alendronate on Rabbit Esophageal Epithelium, Am. J. Physiol. Gastrointest Liver Physiol, Sep. 2002, vol. 283(3): pp. G576-G586.
Grattan et al., A Five Way Crossover Human Volunteer Study to Compare the Pharmacokinetics of Paracetamol Following Oral Administration of Two Commercially Available Paracetamol in Combination with Sodium Tablets Containing Paracetamol in Combination with Sodium Bicarbonate or Calcium Carbonate, European J. of Pharmaceutics and Biopharmaceutics, vol. 49 (2000), pp. 225-229.
Beers, "The Merck Manual of Diagnosis and Therpay" (17th ED) (1999), pp. 250-254.
IPER PCT/US03/33053.
ISR PCT/US03/33053.
ISR PCT/US03/06576.
U.S. Appl. No. 09/722,589, filed Nov. 28, 2000, applicant Ehrenboefer.
U.S. Appl. No. 09/722,590, filed Nov. 28, 2000, applicant Ehrenhoefer.
Gertz, "Studies of the Oral Bioavailability of Alendronate", Sep. 1995, p. 288-298, Clinical Pharmacology & Theraputics, vol. 58, No. 3 St. Louis, MO, US.
Aug. 2010, European Search Report (EP 10 01 0775).

*Primary Examiner* — San-ming Hui
(74) *Attorney, Agent, or Firm* — Neifeld IP Law, P.C.

(57) ABSTRACT

The invention provides effervescent composition comprising a bisphosphonate, an acidic compound, an alkaline effervescing component, and optionally an anti-ulcer agent and methods of treating osteoporosis in a mammal using the effervescent compositions.

6 Claims, No Drawings

EFFERVESCENT COMPOSITIONS COMPRISING PHOSPHONATES AND METHODS RELATED THERETO

CROSS-REFERENCE TO RELATED PATENT APPLICATIONS

This patent application is a continuation of application Ser. No. 10/273,081, filed Oct. 17, 2002, now U.S. Pat. No. 7,488,496, which is a continuation-in-part of U.S. patent application Ser. No. 10/092,083, filed Mar. 6, 2002, abandoned.

TECHNICAL FIELD OF THE INVENTION

The present invention relates generally to effervescent compositions. More particularly, the invention pertains to effervescent compositions comprising a bisphosphonate, and is particularly useful in the treatment of osteoporosis.

BACKGROUND OF THE INVENTION

Osteoporosis is a disease that leads to defective skeletal function caused by low bone mass and deterioration of bone quality. In this respect, bone characterized by weakened mechanical strength is much more susceptible to fracture, even under stresses that would otherwise be tolerated by normal bone. In the United States alone, some 8 million women and 2 million men suffer from osteoporosis. Many more are at increased risk for osteoporosis because they have low bone mass. The risk of suffering from osteoporosis increases with age, particularly in those over the age of 50.

Osteoporosis results from a disorder in bone remodeling, which is the process by which bone tissue is continually renewed and repaired. In bone remodeling, osteoclasts resorb old or damaged bone, while osteoblasts synthesize a new bone matrix. In patients who suffer from osteoporosis, the rate of bone resorption undesirably exceeds the rate of bone formation, either because too much bone is resorbed or too little bone is formed.

Drugs used in the treatment of osteoporosis act by inhibiting bone resorption. Among such anti-resorptive agents are bisphosphonate compounds. Bisphosphonates are synthetic analogues of pyrophosphates, which are naturally occurring regulators of bone turnover.

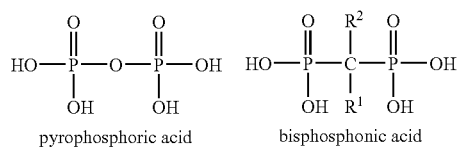

pyrophosphoric acid     bisphosphonic acid

Bisphosphonates, like pyrophosphates, can bind to the surface of the hydroxyapatite bone matrix. It will be appreciated by the ordinarily skilled artisan that the pharmacologic properties of bisphosphonates can be varied through side chain substitutions ($R^1$, $R^2$) on their general chemical structure. For example, alendronate has an amino side chain ($R^2$=$CH_2CH_2CH_2NH_2$) while risedronate has a cyclic nitrogen-containing side chain. The $R^1$ and $R^2$ side chains for a variety of bisphosphonate compounds a given in Table 1.

TABLE 1

| Bisphosphonate | $R^1$ side chain | $R^2$ side chain |
|---|---|---|
| Etidronate | OH | $CH_3$ |
| Clodronate | Cl | Cl |
| Pamidronate | OH | $CH_2CH_2NH_2$ |
| Alendronate | OH | $(CH_2)_3NH_2$ |
| Risedronate | OH | $CH_2$-3-pyridyl |
| Tiludronate | H | $CH_2$—S-phenyl-Cl |
| Ibandronate | OH | $CH_2CH_2N(CH_3)$(pentyl) |
| Zoledronate | OH | $CH_2$-imidazole |
| YH529 | OH | $CH_2$-2-imidazopyridinyl |
| Incadronate | H | N-(cycloheptyl) |
| Olpadronate | OH | $CH_2CH_2N(CH_3)_2$ |
| Neridronate | OH | $(CH_2)_5NH_2$ |
| EB-1053 | OH | $CH_2$-1-pyrrolidinyl |

The oral administration of bisphosphonate compounds for the treatment of osteoporosis suffers from several major drawbacks. First, bisphosphonate compounds are very poorly absorbed from the gastrointestinal tract into the blood of a patient (e.g., have low bioavailability). In fact, typically only about 0.5% to about 5% of the total bisphosphonate active ingredient is absorbed from an oral dosage formulation (e.g., a solid tablet). Once in the blood stream, typically only about 20% to about 50% of the bisphosphonate becomes bound to the bone surface. The bioavailability of bisphosphonate is further reduced under highly acidic gastric conditions, which occur when the patient has eaten food or consumed an acidic beverage (e.g., coffee, tea, or orange juice).

The bioavailability of the bisphosphonate is further affected by the delivery system. Solid delivery systems such as capsules and tablets must be ingested with sufficient liquid to disintegrate the dosage form. Once the dosage form is inside the stomach or small intestine of a patient, it has to disintegrate into small particles, and the active ingredient has to be solubilized such that it can be absorbed into the plasma of the patient. The disintegration and solubilization processes for solid dosage forms delay the bioavailability of the active ingredient.

Effervescent drug formulations can offer enhanced dissolution and absorption of active ingredients resulting in increased bioavailability. Frequently, active ingredients are absorbed better from effervescent formulations as compared to dry, solid tablet formulations. Effervescent tablets also can be larger in size allowing for higher drug loading as well as combination drug loading. Because the tablets are dissolved in water, they are easier to swallow than dry solid tablet formulations. Furthermore, effervescent compositions can be formulated without polyvalent metal ions (e.g., $Ca^{2+}$ and $Mg^{2+}$), which can bind to bisphosphonate compounds rendering them insoluble and unabsorbable. An effervescent bisphosphonate composition is disclosed in U.S. Pat. No. 5,853,759 which describes an effervescent tablet comprising a bisphosphonate, in particular alendronate, an acid component, and an alkaline effervescing component.

A second drawback, even with effervescent formulation, often encountered by patients taking regular dosages of bisphosphonates is the common occurrence of upper gastrointestinal disturbances. Such disturbances include heartburn, esophageal irritation, and even, in some cases, esophageal ulcers. The local tissue irritation and ulceration associated with the administration of bisphosphonates may be mitigated by the administration of drugs that suppress gastric acid production. Anti-ulcer agents such as $H_2$-antagonists (i.e., histamine $H_2$-receptor antagonists) and proton pump inhibitors are known to be effective in combating acid-peptic diseases. Proton pump inhibitors (e.g., $H^+$, $K^+$-ATPase inhibitors) are α-pyridylmethysulfinyl benzimidazole compounds having different pyridine or benzimidazole substituents. The proton pump inhibitors react with acid (are activated) to form thiophilic sulfenamide or sulfenic acid components. Once activated, the compounds irreversibly bind to the sulfhydryl group of cysteine residues thus halting acid production. Commercially available $H_2$-antagonists include cimetidine (Tagamet®), ranitidine (Zantac®), famotidine (Pepcid®), and nizatidine (Axid®). The $H_2$-antagonists inhibit acid production by competing with histamine in binding to $H_2$-receptors.

The combination of these problems has led to a complicated regimen that attempts to optimize bioavailability of the bisphosphonate while minimizing the gastrointestinal problems. Thus, current regimens require the patient to (a) remain strictly upright for at least 30 minutes after taking the bisphosphonate composition so as to minimize esophageal irritation, and (b) wait as much as 2 hours before eating.

U.S. Pat. Nos. 5,994,329, 6,015,801, 6,225,294, and 6,333,316 as well as EP 1 127 573 A1 disclose methods for inhibiting bone resorption comprising sequential administration of histamine $H_2$ receptor blockers and/or proton pump inhibitors about 30 minutes to about 24 hours prior to administration of bisphosphonates. Administration of such histamine $H_2$ receptor blockers and/or proton pump inhibitors in this manner exacerbates the already complicated and inconvenient regimen because the patient would have to take the histamine $H_2$ receptor blockers and/or proton pump inhibitors (e.g. upon waking), then wait 30 minutes or longer to take the bisphosphonate and then wait up to 2 more hours to eat.

Despite the availability of the foregoing approaches, it will be appreciated that there remains a need in the art for compositions and drug administration regimens for osteoporosis, or other bone resorption disorders, which are less complicated and more convenient than those commonly known in the art. Moreover, there remains a need for a composition that can deliver a bisphosphonate drug for treating osteoporosis (or other bone resorption disorders) while reducing associated ulceration. The invention seeks to provide such compositions to satisfy at least one of these needs. These and other advantages of the invention will be apparent from the description of the invention provided herein.

BRIEF SUMMARY OF THE INVENTION

The invention provides an effervescent composition comprising a bisphosphonate, which upon dissolution in water has a buffered pH. In accordance with the present invention, it has been found that including a bisphosphonate in such an effervescent composition imparts improved bioavailability of the bisphosphonate to the body of a mammal. Desirably, the effervescent composition of the invention, when orally administered to a mammal, preferably raises the pH of the gastric juices of the stomach of the mammal to a pH of about 3 or more.

Thus, in one aspect, the present invention provides an effervescent composition comprising a bisphosphonate, an acid component, and an alkaline effervescing component such that the composition, when dissolved in water, produces a solution having a buffered pH of about 3 to about 6.5.

In another aspect the present invention provides an effervescent composition that comprises a bisphosphonate, an anti-ulcer agent, an acid component, an alkaline effervescing component, and optionally a sweetener, a flavorant, or a solubilizing agent.

In yet another aspect, the present invention provides an effervescent composition that comprises a microencapsulated bisphosphonate, an acid component, an alkaline effervescing component, and optionally an anti-ulcer agent.

The present invention also provides a method of inhibiting bone resorption in a mammal. The method comprises combining a bone resorption-inhibiting amount of an effervescing composition according to any aspect of the invention with water to form at least a partial solution, aid administering the solution to the mammal orally.

In another aspect, the present invention provides a method of treating osteoporosis in a mammal. The method comprises combining an osteoporosis-treating effective amount of an effervescing composition according to any aspect of the invention with water to form at least a partial solution, and administering the solution to the mammal orally.

The administration of a bisphosphonate in an effervescent composition to a mammal, in accordance with the present invention, results in improved bioavailability of the bisphosphonate compared to conventional non-effervescent bisphosphonate formulations. As such, if desired, the present invention advantageously can allow for providing a single effervescent composition for delivering the bisphosphonate in combination with an anti-ulcer agent. Furthermore, the bisphosphonate can be present in quantities that are larger than those provided by conventional non-effervescent solid formulations that must be able to be swallowed whole.

The present invention may be best understood with reference to the following detailed description of the preferred embodiments.

DETAILED DESCRIPTION OF THE INVENTION

The present invention is predicated, at least in part, on the surprising and unexpected discovery that a buffered effervescent composition, comprising a bisphosphonate, an acid component, and an alkaline effervescing component, and having a pH of about 3 to about 6.5 when dissolved in water, exhibits improved absorption, and thus improved bioavailability, of the bisphosphonate in the body. In this respect, it is believed that the effervescent composition provides an acid mediating effect on the stomach pH such that the bisphosphonate is more readily absorbed from the intestinal tract into the blood stream.

It has further been found that effervescent compositions comprising both a bisphosphonate and an anti-ulcer agent further enhance the absorption of the bisphosphonate. Pursuant to the present invention, the term "anti-ulcer agent" is defined as including $H_2$ antagonists and/or proton pump inhibitors.

Thus, the effervescent composition according to the invention comprises a bisphosphonate in the inventive effervescent composition and, if desired, may further comprise an anti-ulcer agent. In some embodiments, the effervescent composition comprises a microencapsulated bisphosphonate alone or in combination with an anti-ulcer agent.

The inventive composition advantageously further provides at least one, preferably at least two, and more preferably at least three, of the following properties: quick dissolution upon introduction into water, pleasant taste, clear aqueous composition after dissolution, and acceptable crush resistance after tableting.

The bisphosphonate can be any suitable bisphosphonate. For example, the bisphosphonate can be (4-amino-1-hydroxybutylidene)bisphosphonate (alendronate), [(cycloheptylamino)methylene]bisphosphonate (cimadronate), (dichloromethylene)bisphosphonate (clodronate), [1-hydroxy-3-(1-pyrrolidinyl)-propylidene]bisphosphonate (EB-1053), (1-hydroxyethylidene)bisphosphonate (etidronate), [1-hydroxy-3-(methylpentylamino)propylidene]bisphosphonate (ibandronate), (6-amino-1-hydroxyhexylidene)bisphosphonate (neridronate), [3-(dimethylamino)-1-hydroxypropylidene]bisphosphonate (olpadronate), (3-amino-1-hydroxypropylidene)bisphosphonate (pamidronate), [1-hydroxy-2-(3-pyridinyl)ethylidene]bisphosphonate (risedronate), [[(4-chlorophenyl)thio]methylene]bisphosphonate (tiludronate), [1-hydroxy-2-(imidazo-(1,2a)pyridin-3-yl)ethylidene]bisphosphonate (YH 529), [1-hydroxy-2-(1H-imidazo-1-yl)ethylidene]bisphosphonate (zoledronate), or a combination thereof. Preferably, the bisphosphonate is selected from the group consisting of etidronate, risedronate, alendronate, and combinations thereof. More preferably, the bisphosphonate is alendronate or etidronate.

The effervescent composition can comprise any suitable amount of the bisphosphonate in order to produce an effective blood level of the bisphosphonate in the mammal (e.g., a human) to which the bisphosphonate is administered. Typically, about 0.1% or more (e.g., about 0.25% or more or about 1% or more) bisphosphonate, based on the total weight of the composition, is present in the effervescent composition. For example, the effervescent composition can comprise about 0.25% to about 33.3% bisphosphonate, based on the total weight of the composition. In some embodiments, about 1.5% or more (e.g., about 3% or more or about 5% or more) and about 30% or less (e.g., about 20% or less) bisphosphonate, based on the total weight of the composition, is present in the effervescent composition. The effervescent composition can be administered to a mammal following a continuous dosing schedule. The continuous schedule can be daily, once weekly, twice weekly, thrice weekly, biweekly, monthly, or every other month.

The actual amount of bisphosphonate present in the effervescent composition depends at least in part on the specific bisphosphonate and the dosing schedule chosen. When the bisphosphonate is alendronate, typically about 1 mg or more and about 500 mg or less bisphosphonate is present, preferably about 5 mg to about 200 mg. When the bisphosphonate is risedronate, typically about 1 mg or more and about 200 mg or less bisphosphonate is present, preferably about 2 mg to about 50 mg. When the bisphosphonate is etidronate, typically about 70 mg or more and about 2000 mg or less bisphosphonate is present preferably about 100 mg to about 500 mg (e.g., about 200 mg to about 400 mg). When the bisphosphonate is tiludronate, typically about 50 mg or more and about 1000 mg or less bisphosphonate is present, preferably about 100 mg to about 500 mg. When the bisphosphonate is ibandronate, typically about 0.1 mg or more and about 200 mg or less bisphosphonate is present, preferably about 1 mg to about 50 mg.

Moreover, if the absorption of the active agents into the blood stream is improved (e.g., by 3 times, 5 times, or even 10 times) through die use of the effervescent composition of the invention versus a traditional tablet or capsule formulation containing the same amount of the active agent, the amount of the active agent present in the effervescent composition can be reduced from the amount required in tablet or capsule formulations (e.g., the amounts set forth above). Thus, the effervescent composition of the invention optionally may contain only 35 wt. % or less (e.g., about 25 wt. %, or even about 15 wt. % or less) than the amount by weight of active agent required in traditional tablet or capsule formulations without changing the amount of the active agent present in the bloodstream of the mammal. The ability to reduce the amount of active bisphosphonate a dosage form without reducing the amount absorbed into the bloodstream of the mammal is a significant step towards reducing the overall cost of the dosage form.

For example, when the bisphosphonate is administered weekly, twice weekly, biweekly, monthly or every oilier month, preferably the amount of bisphosphonate present in the effervescent composition is less than that required for tablet formulations for similar dosage schedules. When the bisphosphonate is alendronate, typically the weekly dosage is only about 8 mg to about 16 mg, preferably about 10 mg to about 15 mg. The monthly dosage of alendronate typically is about 30 mg to about 200 mg, preferably about 50 mg to about 120 mg. The dosage for every other month administration of alendronate typically is about 50 mg to about 500 mg, preferably about 100 mg to about 300 mg. When the bisphosphonate is etidronate, the monthly dosage typically is about 400 mg to about 800 mg, preferably about 500 mg to about 700 mg. The dosage for every other month administration of etidronate typically is about 800 mg to about 1600 mg, preferably about 1000 mg to about 1500 mg. When the bisphosphonate is ibandronate, the monthly dosage typically is about 50 mg to about 90 mg, preferably about 60 mg to about 85 mg. The dosage for every other month administration of ibandronate typically is about 100 mg to about 300 mg, preferably about 125 mg to about 250 mg. When the bisphosphonate is residronate, the monthly dosage typically is about 20 mg to about 140 mg, preferably about 50 mg to about 100 mg. The dosage for every other month administration of etidronate typically is about 100 mg to about 300 mg, preferably about 120 mg to about 200 mg.

Currently approved dosage regimens for alendronate include 5 mg or 10 mg once daily and 35 mg or 70 mg once weekly for treatment of osteoporosis. For treatment of Paget's disease, the recommended dosage regimen is 40 mg once daily. Currently approved dosage regimens for risedronate include 5 mg once daily and 35 mg once weekly for treatment of osteoporosis. Currently approved dosage regimens for etidronate include 400 mg once daily (5-20 mg/g/day) over six months for treatment of Paget's disease. Currently approved dosage regimens for tiludronate include 400 mg once daily over 3 months for treatment of Paget's disease. All dosage amounts stated herein are in terms of the free bisphosphonic acid.

The bisphosphonate can be finely milled to enhance the absorption of the bisphosphonate. In this respect, such finely milled particles of the bisphosphonate result in more surface area being exposed to the absorption medium, thereby maximizing absorption. Desirably, the bisphosphonate is milled to a particle size of about 100 microns or less (e.g., about 4 microns to about 100 microns). Preferably, the bisphosphonate is milled to a particle size of about 5 microns to about 70 microns (e.g., about 10 microns to about 50 microns).

The acid component can be any suitable acid component. Typically, the acid component is an organic or mineral acid that is safe for consumption and which provides for effective and rapid effervescent disintegration upon contact with water and the alkaline effervescent component. For example, the acid component can be selected from the group consisting of citric acid, tartaric acid, malic acid, fumaric acid, adipic acid, succinic acid, acid anhydrides, acid salts (e.g., sodium salts and potassium salts), mixtures of acid salts; acid salts of disodium dihydrogen pyrophosphate, acid citrate salts (e.g., monosodium citrate and disodium citrate) and other related organic acids and their salts, and combinations thereof. Preferably, the acid component comprises citric acid (e.g., citric acid anhydrous) and optionally any of the other acid components described above (e.g. an organic acid or salt, preferably monosodium citrate and/or monopotassium citrate). The use of non-sodium acid components is desirable for use with patients requiring electrolyte maintenance, e.g., hypertensive and other cardiac patients.

The alkaline effervescing component can be any suitable alkaline effervescent component. Typically, the alkaline effervescing component is an organic or mineral based (e.g., alkali metal carbonate) that is safe for consumption and provides effective and rapid effervescent disintegration upon contact with water and the acid component. For example, the alkaline effervescing component can be selected from the group consisting of carbonate salts, bicarbonate salts, and mixtures thereof. Preferably, the alkaline effervescing component is selected from the group consisting of sodium bicarbonate, sodium carbonate anhydrous, potassium carbonate, and potassium bicarbonate, sodium glycine carbonate, calcium carbonate, calcium bicarbonate, L-lysine carbonate, arginine carbonate, and combinations thereof. In some embodiments, the alkaline effervescing component is sodium bicarbonate, potassium bicarbonate, sodium carbonate, or a combination thereof.

More preferably, the alkaline effervescing component comprises a carbonate salt, a bicarbonate salt, and optionally another suitable alkaline effervescing components as described above. The carbonate salt can be any suitable carbonate salt and typically is selected from the group consisting of sodium carbonate, potassium carbonate, and combinations thereof. The bicarbonate salt can be any suitable bicarbonate salt and typically is selected from the group consisting of sodium bicarbonate, potassium bicarbonate, and combinations thereof. The use of non-sodium alkaline effervescing components is desirable for use with patients requiring electrolyte maintenance, e.g., hypertensive and other cardiac patients.

The acid component and the alkaline effervescent component can be present in the effervescent composition in any suitable amount. The relative amounts of acid component and alkaline effervescent component are such that the effervescent composition, when dissolved in water, produces a butter solution. For the purposes of clarity, by the phrase "effervescent composition completely dissolves" it is meant that the acid component and the alkaline effervescent component are completely dissolved in the water, even though another components (e.g., the bisphosphonate or a microencapsulated bisphosphonate) are not completely dissolved or not at all dissolved. The buffer solution is produced when the acid component reacts with the alkaline effervescent component to produce a solution containing the acid component and/or the alkaline effervescent component in equilibrium with the fully deprotonated salt of the acid component. For example, when the acid component is citric acid and the alkaline component is sodium bicarbonate, the buffer would consist of an acid form of citric acid and sodium citrate (e.g., the fully deprotonated salt of citric acid). Typically, the buffered solution has a pH of about 3 to about 6.5 (e.g., about 3.5 to about 6.5 or about 4 to about 6.5). Preferably, the buffered solution has a pH of about 3.5 to about 6 (e.g., about 4 to about 6). More preferably, the buffered solution has a pH of about 4 to about 5.5 (e.g., 4.5 to about 5.5). For example, in some embodiments the buffered solution contains an amount of fully deprotonated salt of the acid component that is at least about 1.5 times (e.g., at least about 1.75 times or at least about 2 times) the amount of acid equivalents (e.g., equivalents of acid groups within the acid component). In some embodiments, the amount of acid equivalents is non-zero.

Desirably, the acid component is present in the effervescent composition in an amount of about 25% to about 75% based on the total weight of the composition and the alkaline effervescing component is present in the effervescent composition in an amount of from about 20% to about 60% based on the total weight of the composition. In a preferred embodiment, the amount of citric acid may be less than about 20% (e.g., about 1% to about 15%, or about 5% to about 10%) based on the total weight of the acid component and the alkaline effervescing component. The amount of carbonate salt may be less than about 20% (e.g., about 0.1% to about 10%, or about 1% to about 7%) based on the total weight of the acid component and the alkaline effervescing component. The amount of bicarbonate salt may be less than about 60% (e.g., about 25% to about 50%, or about 30% to about 45%) based on the total weight of the acid component and the alkaline effervescing component.

Preferably, the weight ratio of bicarbonate to carbonate salt should be controlled to provide optional performance of the effervescent formulation. In this regard, it is advantageous that the amount of bicarbonate salt may be at least about 4 times (e.g., preferably at least about 6 times, or more preferably at least about 8 times) the amount by weight of carbonate salt. In an especially preferred embodiment, the effervescent composition comprises about 1% to about 15% citric acid, about 35% to about 60% monosodium citrate, about 0.1% to about 10% carbonate salt, and about 25% to about 50% bicarbonate salt, based on the total weight of the acid component and the alkaline effervescing component.

Advantageously, the inventive effervescent composition may comprise a bisphosphonate, an acid component comprising about 1% to about 15% citric acid by weight based on the total weight of the acid component and the alkaline effervescing component, and an alkaline effervescing component comprising about 0.1% to about 10% by weight carbonate salt and about 25% to about 50% by weight bicarbonate salt based on the total weight of the acid component and the alkaline effervescing component, the effervescent composition, when dissolved in water, providing an aqueous composition having a buffered pH of about 3 to about 6.5 (e.g., about 4 to about 6.5, or about 5 to about 6.5). Such a composition may preferably further include the weight ratios of bicarbonate salt to carbonate salt described above.

Desirably, administration of the buffer solution produced upon dissolution of the effervescent composition in water to a mammal (e.g., a patient) produces a stomach pH in the mammal of at least about 3 or greater (e.g., about 3.5 or greater), more preferably about 4 or greater (e.g., about 4.5 or greater). The buffer solution typically is capable of mediating the pH of a patient's stomach for at least about 10 minutes or more (e.g., about 15 minutes or more). In some embodiments, the buffer solution is capable of mediating the pH of a patient's stomach for up to about 30 minutes or more (e.g., up to about 45 minutes or more).

In one embodiment, the effervescent composition optionally further comprises an anti-ulcer agent. The anti-ulcer agent can be an $H_2$-antagonist, a proton pump inhibitor, or a combination thereof. The $H_2$-antagonist can be any suitable $H_2$-antagonist. For example, the $H_2$-antagonist can be ranitidine, cimetidine, famotidine, nizatidine, or a combination thereof. Preferably, the $H_2$-antagonist is ranitidine or cimetidine. Typically, the $H_2$-antagonist is present in the effervescent composition in al amount of about 3.3% to about 57.5% (e.g., about 8% to about 40%) based on the total weight of the composition. The $H_2$-antagonist preferably is present in the effervescing composition in an amount of about 5 mg to about 500 mg, depending on the specific antagonist selected. By way of example, when the $H_2$-antagonist is ranitidine, the composition comprises about 25 mg to about 300 mg (e.g., about 50 mg to about 200 mg) $H_2$-antagonist; when the $H_2$-antagonist is cimetidine, the composition comprises about 25 mg to about 400 mg (e.g., about 50 mg to about 350 mg) $H_2$-antagonist; when the $H_2$-antagonist is famotidine, the composition comprises about 2 mg to about 50 mg (e.g., about 5 mg to about 30 mg) $H_2$-antagonist; and when the $H_2$-antagonist is nizatidine, the composition comprises about 25 mg to about 350 mg (e.g., about 50 to about 300 mg) $H_2$-antagonist.

The anti-ulcer agent comprises any suitable proton pump inhibitor. By way of example, the proton pump inhibitor can be omeprazole, lansoprozole, rabeprazole, pantoprazole, or a combination thereof. Preferably, the proton pump inhibitor is omeprazole. Typically, the proton pump inhibitor is present in an amount of from about 0.5% to about 60% by weight of the composition (e.g., about 5% to about 40%). The proton pump inhibitor is present in the effervescing composition in an amount of about 5 mg to about 100 mg, depending on the specific proton pump inhibitor used. For example, when the proton pump inhibitor is omeprazole, the composition comprises about 10 mg to about 30 mg proton pump inhibitor; when the proton pump inhibitor is lansoprazole, the composition comprises about 2 mg to about 30 mg (e.g. about 5 mg to about 20 mg) proton pump inhibitor; when the proton pump inhibitor is rabeprazole, the composition comprises about 5 mg to about 60 mg (e.g., about 10 to about 45 mg) proton pump inhibitor; and when the proton pump inhibitor is pantoprazole, the composition comprises about 5 mg to about 50 mg (e.g., about 10 mg to about 35 mg) proton pump inhibitor.

When the effervescent composition comprises one of the anti-ulcer agents described above, the capacity of the buffer solution to mediate the pH of a patient's stomach typically is extended beyond that of the effervescent composition without the anti-ulcer agent. For example, the dissolved solution is able to mediate the pH of a patient's stomach for up to about 60 minutes or more (e.g., up to about 90 minutes or more or up to about 120 minutes or more).

The effervescent composition of the invention desirably has a pleasing taste. The taste of a pharmaceutical composition is important as it enhances the willingness of patients to utilize the dosage form. Many active agents, such as bisphosphonates and anti-ulcer agents, have an objectionable taste that must be masked by the formulation in which the active agents are delivered. Therefore, the effervescent composition preferably comprises a sweetener, a flavorant, or a combination thereof. It was also found that the effect of the latter is enhanced relative to known effervescent compositions due to the inventive nature of the present effervescent composition. In some embodiments, the effervescent composition comprises both a sweetener and a flavorant.

The sweetener can be any suitable natural or artificial sweetener or a combination of natural and artificial sweeteners. Acceptable natural sweeteners include members selected from the group of glucose, dextrose, inert sugar, fructose, glycyrrhizic acid, and mixtures thereof. Typically, the natural sweetener is present in the effervescent composition in an amount of about 10% to about 50% (e.g., about 20% to about 40%) based on the weight of the composition. Acceptable artificial sweeteners include members selected from the group consisting of saccharin; aspartame; chloro-derivatives of sucrose such as sucralose, cyclamate, acesulfame-K; sugar alcohols such as sorbitol, mannitol, and xylitol; and mixtures thereof. Typically, the artificial sweetener is present in the effervescent composition in an amount of about 0 to about 5% (e.g., about 0.1 to about 2.5%) based on the weight of the composition. Preferably, the sweetener is an artificial sweetener selected from the group consisting of aspartame, saccharin, acesulfame-K, xylitol, Splenda®, and combinations thereof. The effective concentration of a sweetener is determined by the strength of its sweetness, solubility, and masking ability for a specific active ingredient(s). For example, when the sweetener is aspartame, about 10 mg to about 50 mg aspartame is present in the effervescent composition. When the sweetener is saccharin, about 10 mg to about 30 mg saccharin is present in the effervescent composition. When the sweetener is acesulfame-K, about 10 mg to about 50 mg acesulfame-K is present in the effervescent composition. When the sweetener is xylitol, about 100 mg to about 400 mg xylitol is present in the effervescent composition. When the sweetener is Splenda®, about 10 mg to about 50 mg Splenda® is present in the effervescent composition.

The flavorant can be a natural or synthetic flavorant. Typically, the flavorant is present in the effervescent composition in an amount of about 0% to about 10% (e.g., about 1% to about 7.5%) based on the weight of the composition. Acceptable flavorants include members selected from the group consisting of volatile oils, synthetic flavor oils, oleoresins, plant extracts (e.g., green tea flavor), and combinations thereof. Desirable flavorants include a member selected from the group consisting of citrus oils such as lemon, orange, grape, lime and grapefruit; fruit essences such as apple, pear, peach, grape, strawberry, raspberry, cherry, plum, pineapples, and apricot; and other fruit flavors. Other useful flavorants include aldehydes and esters such as benzaldehyde (cherry, almond), citral (lemon, lime), neral (lemon, lime), decanal (orange, lemon), $C_8$-aldehyde (citrus fruits), $C_9$-aldehyde (citrus fruits), $C_{12}$-aldehyde (citrus fruits), tolylaldehyde (cherry, almond), 2,6-dimethyloctanal (green fruit), and 2-dodecenal (citrus, mandarin), and mixtures thereof. Preferably, the flavorant is cherry, citrus, or orange. The flavorant typically is present in the effervescent composition in an amount of about 10 mg to about 100 mg.

The pH range of the buffered aqueous composition resulting from dissolution of the effervescent composition is desirably in the range of about 3 to about 6.5 (e.g., about 4 to about 6.5) or about 5 to about 6.5). In order to avoid decomposition of many acid-sensitive active agents, it is necessary to remain at a pH above the pKa of the active agent, preferably a pH that is at least 0.7 pH units above the pKa, or even 1 pH unit above the pKa of the active agent. For example, when the effervescent composition comprises an anti-ulcer agent, such as omeprazole, it is desirable to remain at a pH above the pKa of the anti-ulcer agent. The pKa of omeprazole is about 3.9, thus an effervescent composition of the invention comprising omeprazole desirably has a buffered pH of at least about 5. The upper limit for the buffer pH is ultimately limited by the tolerance of the stomach lining for alkaline solutions. Typically the upper limit of the stomach tolerance is about 10. However, the upper pH limit may further be limited by the pH tolerance of the ingredients included in the effervescent formulation. For example, the perceived flavor of a flavorant or sweetener can be affected by the pH of the buffered solution. Many flavorants undergo a chemical change causing the flavorants to lose or change their flavor at alkaline pH values (e.g., at pH values of about 7 or higher, or about 7.5 or higher). Thus, it has been found that selection of an appropriate buffered pH range for the effervescent composition of the invention requires a delicate balance of the pH considerations of the active agent (e.g., bioavailability and stability), as well as the considerations of the stomach tolerance and stability of inactive ingredients such as flavorants and sweeteners that are responsible for taste-masking.

The effervescent composition optionally further comprises a solubilizing agent, which aids in the transition of the bisphosphonate from the gastrointestinal tract to the blood by solubilizing the bisphosphonate and facilitating its transfer into the mucosal interface of the gastrointestinal tract. The solubilizing agent can be any suitable solubilizing agent. For example, the solubilizing agent can be a polyvinylpyrrolidone, a polyethylene glycol, a dextran, or a combination thereof. The polyvinylpyrrolidone and polyethylene glycol can have any suitable molecular weight. For example, the polyvinylpyrrolidone can have a molecular weight of about 20,000 g/mol to about 40,000 g/mol, preferably about 25,000 g/mol to about 35,000 g/mol, more preferably about 28,000 g/mol to about 32,000 g/mol. The polyethylene glycol can have a molecular weight of about 2000 g/mol to about 10,000 g/mol (e.g., about 4000 g/mol, about 6000 g/mol, or about 8000 g/mol). The dextran can be any suitable branched poly-D-glucoside having predominantly $C_{1-6}$ glycosidic bonds. In some embodiments, the solubilizing agent comprises both polyvinylpyrrolidone and polyethylene glycol. Typically, the solubilizing agent is present in the effervescent composition in an amount of from about 0.1% or more based on the weight of the composition. For example, about 0.1% to about 10% (e.g., about 1% to about 5%) based on the weight of the composition polyvinylpyrrolidone and/or about 20 mg to about 100 mg polyethylene glycol can be present in the effervescent composition. When the solubilizing agent is a dextran, about 1% to about 20%, preferably about 5% to about 15% (e.g., about 10%) dextran based on the weight of the composition can be present in the effervescent composition.

In one embodiment, the effervescent composition comprises a bisphosphonate, an anti-ulcer agent, an acid component, an alkaline effervescing component, and, optionally, one or more ingredients selected from sweeteners, flavorants, and solubilizing agents. Typically, the effervescent composition comprises about 0.1% to about 19% bisphosphonate, about 0.5% to about 50% anti-ulcer agent, about 15% to about 60% acid component, about 20% to about 70% alkaline effervescing component, about 0% to about 5% sweetener, about 0% to about 10% flavorant, and about 0% to about 10% solubilizing agent. Preferably, the effervescent composition comprises about 0.5% to about 10% bisphosphonate, about 2% to about 30% anti-ulcer agent, about 25% to about 45% acid component, about 30% to about 60% alkaline effervescing component, about 2% to about 4% sweetener, about 3% to about 8% flavorant, and about 1% to about 5% solubilizing agent. The percent amounts recited above are based on the total weight of the effervescent composition.

In another embodiment, the effervescent composition comprises a bisphosphonate compound that is encapsulated (e.g., microencapsulated) in a time-release (e.g., sustained-, delayed- or directed-release) delivery system. The encapsulation of the bisphosphonate is preferred when delayed release of the active ingredient into the stomach is desired, for example, when the bisphosphonate is administered simultaneously with an $H_2$-antagonist or a proton pump inhibitor. Encapsulation of the bisphosphonate could minimize or eliminate irritation of the esophagus of the patient and other patient distress such as nausea. Encapsulation of the bisphosphonate also could delay release of the bisphosphonate until the stomach absorbs the anti-ulcer agent and inhibition of the stomach's acid production has begun. The encapsulation could delay release of the bisphosphonate by about 2 to about 30 minutes, preferably by about 5 to about 10 minutes. It is to be noted that effervescent compositions comprising encapsulated bisphosphonate, when dissolved in water, achieve the desired buffered pH in accordance with the invention. In this respect, the acid component and the alkaline effervescent component are completely dissolved but, of course, the encapsulated bisphosphonate remains encapsulated.

The bisphosphonate can be encapsulated in any suitable manner as will be readily appreciated by one of ordinary skill in the art. For example, the polymer coating can be any suitable differentially degrading coating including microencapsulation, enteric coating, multiple coating, and the like. The polymer coating may be one that resists disintegration upon contact with the saliva but instantly releases the bisphosphonate upon contact with gastric juice in the stomach. Alternatively, the polymer coating may be one that resists rapid disintegration in the presence of gastric juice. Suitable coating polymers include biodegradable polymers such as polylactic acid, polyglycolic acid, copolymers of lactic and glycolic acid, polyorthoesters, and polyanhydrides thereof. The bisphosphonate also can be encapsulated by a polymer coating such as a cellulosic (e.g., methyl or ethyl cellulose) coating, a wax coating, a gum coating, or within a liposomal delivery system. Suitable methods of preparing effervescent compositions containing microencapsulated active ingredients are described, for example, in U.S. Pat. Nos. 4,462,982, 4,710,384, 5,178,878, and 5,709,886. Preferably, the microencapsulated bisphosphonate has a mean particle size of about 25 microns to about 120 microns (e.g., about 40 microns to about 70 microns). More preferably, the microencapsulated bisphosphonate has a mean particle size of about 50 microns.

The effervescent compositions described above optionally further comprise a colorant. The colorant can be any suitable colorant including natural colorants, food, drug and cosmetics (FD&C) colorants, and drug and cosmetic (D&C) colorants. Suitable natural colorants include red beet powder and beta-carotene powder.

The effervescent compositions described above optionally further comprise other ingredients to aid in the formulation of the composition and/or for aesthetic purposes. Such other ingredients include, for example, fragrances, dyes, filters such as calcium sulfate, starch, and binders. Desirable binders assist in tablet compression and can include starches, pregelatinized starches, gelatin, methylcellulose, sodium carboxymethylcellulose, ethylcellulose, polyacrylamides, polyvinyloxoazolidone, polyvinylalcohols, and polyvinylpyrrolidone.

The effervescent compositions described above optionally further comprise a disintegrant to enhance the disintegration of the compressed tablet in water. The disintegrant can be any suitable disintegrant. For example, the disintegrant can be starch, alginic acid, guar gum, kaolin, bentonite, sodium starch glycolate, isoamorphous silicate, and microcrystalline cellulose.

The effervescent compositions described above optionally ter comprise a lubricant, which is applied to dies before the granular mixture is compressed into the effervescent tablet. Lubricants can include hydrogenated or partially hydrogenated vegetable oils such as corn oil, canola oil, cottonseed oil, sesame oil, soybean oil, grape seed oil, sunflower oil, safflower oil, olive oil, peanut oil, and combinations thereof. Lubricants can also include calcium stearate, magnesium stearate, zinc stearate, polyoxyethylene monostearate, talc, polyethyleneglycol, sodium benzoate, sodium lauryl sulfate, magnesium lauryl sulfate, light mineral oil, and combination thereof. Lubricants can form a hydrophobic coating on an effervescent tablet and affect the dissolution rate of the tablet. The preferred embodiment of the invention uses paraffin oil or magnesium stearate as a lubricant. Paraffin oil or magnesium stearate dust imparts desirable dissolution characteristics to the tablets and facilitates the high-speed production of the tablets.

The effervescent compositions described above can be formulated as a tablet, granulate, or a powder. Suitable methods for producing the effervescent compositions of the invention include those described in U.S. Pat. Nos. 4,687,662, 4,942,039, 5,348,745, 5,415,870, 5,480,652, 5,853,759, and 6,284,272. Preferably, the acid component and the alkaline effervescing component are at least partially reacted with each other during granulation with the bisphosphonate.

Typically the effervescent compositions of the invention have a total weight of about 1500 mg or more (e.g., about 2000 mg or more). In some embodiments, the effervescent composition has a total weight of about 2500 mg or more. Preferably, effervescent compositions have a total weight of about 2000 mg to about 6000 mg (e.g., about 3500 mg to about 5000 mg).

The effervescent composition of the invention, when formulated as a tablet, desirably has a disintegration time of about 180 s or less (e.g., advantageously about 150 s or less, or preferably about 120 s or less) upon contact with about 60 ml of water. More preferably, the disintegration time of the effervescent tablet is about 90 s or less, and most preferably about 60 s or less. The disintegration time depends, at least in part, on the relative amounts of the "fast-reacting components" to the "slow-reacting components." Citric acid and carbonate salts react very fast with alkaline compounds and acid compounds, respectively, upon dissolution in water. Other effervescent components like monosodium citrate and bicarbonate salts react a bit slower with alkaline compounds and acid compounds, respectively, upon dissolution in water. It has been discovered that by balancing the relative amounts of the fast-reacting compounds to the slow-reacting compounds, an effervescent composition can be produced which has a fast disintegration time and, preferably also provides a clear solution that is substantially free or totally free of undissolved acid or alkaline effervescent components. Clear solutions are more aesthetically pleasing to patients than solutions containing suspended particles that can be seen by the naked eye.

The effervescent composition of the invention typically has an acid neutralizing capacity (ANC) of about 10 mEq or more of HCl. Preferably, the effervescent composition of the invention typically has an ANC of about 12 mEq or more (e.g., about 13 to about 20 mEq HCl). The ANC can be determined by inflection point titration (IPT) method or by a Gran function plot method. IPT involves plotting the pH of a solution of the effervescent composition as a function of the volume of strong acid added and identifying the tinflection point of the titration. The Gran function plot method involves plotting a Gran function (e.g., the sum of the initial volume ($V_o$) and volume acid added ($V_i$) multiplied by the antilog of the change in pH (i.e., $[(V_o+V_i)(10^{-pH})]$) versus the volume of acid added ($V_i$) and fitting a line through the data points (e.g., by regression analysis). The ANC value is determined by multiplying the normality of the acid by the linear constant (i.e., the point at which the line crosses the x-axis), and dividing by the sample volume.

The effervescent compositions of the invention preferably are used in a method of treating and/or preventing conditions or disease states in a mammal involving excessive bone resorption related to bone formation. Such disease states including osteoporosis (e.g., post-menopausal osteoporosis, steroid-induced osteoporosis, male osteoporosis, disease-induced osteoporosis, idiopathic osteoporosis), Paget's disease, abnormally increase bone turnover, periodontal disease, localized bone loss from periprosthetic osteolysis, and bone fractures.

In one embodiment, the effervescent compositions are used in a method of inhibiting bone resorption in a mammal. The treatment comprises combining a bone resorption inhibiting amount of the effervescent composition with water to form at least a partial solution and administering the solution to the mammal (e.g., patient) orally.

In another embodiment, the effervescent compositions are used in a method of treating osteoporosis in a mammal. The treatment method comprises combining an osteoporosis-treating effective amount of the effervescent composition with water to form at least a partial solution and administering the solution to the mammal (e.g., patient) orally.

The administration of the effervescent composition to the mammal preferably causes the pH of the contents of the mammal's stomach (e.g., the gastric juices) to be raised to a pH of about 3 or greater. More preferably, the administration of the effervescent composition to the mammal causes the pH of the mammal's stomach to be raised to a pH of about 3.5 or greater (e.g., about 4 or greater). Typically, the pH of the mammal's stomach is not raised above about 6.5 (e.g., not above about 6).

The following examples further illustrate the invention but, of course, should not be construed as in any way limiting its scope.

EXAMPLE 1

This example illustrates a process for preparing the effervescent tablets of the invention, comprising etidronate and an $H_2$-antagonist (anti-ulcer agent), using a wet granulation method.

An effervescent tablet of etidronate is formed from the ingredients listed in Table 2.

TABLE 2

| Ingredient | Amount | Function |
| --- | --- | --- |
| etidronate | 70 to 800 mg | active bisphosphonate |
| cimetidine | 100 to 400 mg | anti-ulcer agent |
| citric acid | 800 to 1600 mg | acid component |
| sodium bicarbonate | 800 to 1600 mg | alkaline effervescing cmpd |
| potassium bicarbonate | 0 to 800 mg | alkaline effervescing cmpd |
| sodium carbonate | 20 to 100 mg | alkaline effervescing cmpd |
| polyvinylpyrrolidone | 1 to 5 wt. % by wt | solubilizer |
| polyethylene glycol 6000 | 20 to 100 mg | solubilizer |
| aspartame | 10 to 50 mg | sweetener |
| raspberry flavor | 10 to 100 mg | flavorant |

All process steps for this example are performed under approximately 20% relative humidity. The etidronate, cimetidine, polyvinylpyrrolidone, a part of the citric acid, a part of the sodium bicarbonate, a part of the potassium bicarbonate, a part of the sodium carbonate, and a part of the polyethylene glycol are homogeneously mixed in a high-speed mixer. The powders are wetted with a small amount of water. This vetting initiates a slight effervescent reaction between the acidic and the alkaline components. This effervescent reaction binds the components together with the polyvinylpyrrolidone. The wetted powders are dried with heat in a vacuum at a very low humidity until the powder achieves approximately 0.15% loss on drying. After sieving for particle size the dried granulate is mixed in a tumbler with the remaining ingredients.

The tablet mixture is compressed on a suitable commercially available rotary tablet press. The dies are lined with nylon inserts and/or lubricated with a thin film of paraffin oil or magnesium stearate, which is applied by spraying. The tablets are filled on-line into tubes or strips.

EXAMPLE 2

This example illustrates a process for preparing the effervescent tablets of the invention, comprising etidronate and an $H_2$-antagonist (anti-ulcer agent), using a wet granulation method.

The ingredients listed in Table 3 are used in the production of an effervescent tablet of the invention.

TABLE 3

| Ingredient | Amount Range (in mg) | Actual Amount (in mg) |
| --- | --- | --- |
| etidronate | 70-800 | 200 |
| cimetidine | 100-400 | 250 |
| citric acid | 800-1600 | 1400 |
| sodium bicarbonate | 800-1600 | 800 |
| potassium bicarbonate | 0-800 | 695 |
| sodium carbonate | 20-200 | 160 |
| polyvinylpyrrolidone | 1-5 wt. % | 2 wt. % |
| aspartame | 10-50 | 20 |
| saccharin | 10-30 | 20 |
| polyethylene glycol 6000 | 20-100 | 60 |
| flavorant | 10-100 | 25 |
| colorant | 0-10 | 5 |

The etidronate, polyvinylpyrrolidone, and sodium bicarbonate are premixed. The colorant, cimetidine, and sodium carbonate are premixed. Place the citric acid in a bowl of a suitable blender. Add a sufficient amount of water to the citric acid slowly and mix thoroughly to form a moist blend. Add to the blend, in sequence, while mixing, the sodium bicarbonate mix and the sodium carbonate mix until uniformly distributed. While mixing, the polyethylene glycol is added and the mixture is blended until uniformly distributed.

The tablet mixture is compressed on a suitable commercially available rotary tablet press. The dies are lined with nylon inserts and/or lubricated with a thin film of paraffin oil or magnesium stearate, which is applied by spraying. The tablets are filled on-line into tubes or strips.

EXAMPLE 3

This example illustrates a process for preparing the effervescent tablets of the invention, comprising etidronate and an proton pump inhibitor (anti-ulcer agent), using a wet granulation method.

The ingredients listed in Table 4 are used in the production of an effervescent tablet of the invention.

TABLE 4

| Ingredient | Actual Amount (in mg) |
| --- | --- |
| etidronate | 200 |
| omeprazole | 20 |
| citric acid | 420 |
| sodium citrate monobasic | 1820 |
| potassium-sodium tartrate | 5 |
| sodium bicarbonate | 800 |
| potassium bicarbonate | 695 |
| sodium carbonate | 160 |

TABLE 4-continued

| Ingredient | Actual Amount (in mg) |
| --- | --- |
| polyvinylpyrrolidone | 2 wt. % |
| aspartame | 30 |
| polyethylene glycol 8000 | 45 |
| flavorant | 50 |
| colorant | 5 |

Blend etidronate, omeprazole, citric acid, sodium citrate monobasic, potassium sodium tartrate, polyvinylpyrrolidone, polyethylene glycol, and aspartame in a suitable blender. Quickly add all of water and mix until a workable mass is formed. Granulate through a suitable screen using a granulator. Spread evenly on a paper-lined tray or a fluid bed dryer. Place a dried granulation in a suitable blender and add powder sodium bicarbonate, potassium bicarbonate, and sodium carbonate. Mix well. Add flavorant and colorant and mix until uniformly distributed.

The tablet mixture is compressed on a suitable commercially available rotary tablet press. The process is carried out at room temperature and with a relative humidity not higher than 15-20%. The dies are lined with nylon inserts and/or lubricated with a thin film of paraffin oil or magnesium stearate, which is applied by spraying. The tablets are filled on-line into tubes or strips.

The tablet when dissolved in 120 ml water produces a solution having a buffered pH of about 5.5 to about 6.0.

EXAMPLE 4

This example illustrates a process for preparing the effervescent tablets of the invention, comprising etidronate and an $H_2$-antagonist (anti-ulcer agent), using a dry granulation method.

The ingredients listed in Table 5 are used in the production of an effervescent tablet of the invention.

TABLE 5

| Ingredient | Actual Amount (in mg) |
| --- | --- |
| etidronate | 200 |
| ranitidine | 200 |
| citric acid | 525 |
| sodium citrate monobasic | 1820 |
| Potassium-sodium tartrate | 5 |
| Sodium bicarbonate | 800 |
| potassium bicarbonate | 695 |
| sodium carbonate | 40 |
| polyvinylpyrrolidone | 2 wt. % |
| Splenda ® | 30 |
| polyethylene glycol 8000 | 45 |
| flavorant | 50 |
| colorant | 5 |

Etidronate, ranitidine, polyethylene glycol, and polyvinylpyrrolidone are blended in a suitable mixer until uniform. To the mixture are added citric acid, potassium sodium tartrate, and sodium citrate monobasic, alternating with sodium bicarbonate, potassium bicarbonate, and sodium carbonate. After all the acidic and alkaline components are added, add the remaining ingredients and mix until uniform. Roller compact the powder mix followed by granulation using a suitable screen.

The tablet mixture is compressed on a suitable commercially available rotary tablet press. The process is carried out at room temperature and with a relative humidity not higher than 15-20%. The dies are lined with nylon inserts and/or lubricated with a thin film of paraffin oil or magnesium stearate, which is applied by spraying. The tablets are filled on-line into tubes or strips.

The tablet when dissolved in 120 ml water produces a solution having a buffered pH of about 3.0 to about 3.4.

EXAMPLE 5

This example illustrates a process for preparing the effervescent tablets of the invention, comprising etidronate and a proton pump inhibitor (anti-ulcer agent), using a two-part dry granulation method.

The ingredients listed in Table 6 are used in the production of an effervescent tablet of the invention.

TABLE 6

| Ingredient | Actual Amount (in mg) |
| --- | --- |
| Etidronate | 200 |
| Lansoprazole | 15 |
| citric acid | 475 |
| sodium citrate monobasic | 1820 |
| potassium sodium tartrate | 5 |
| sodium bicarbonate | 800 |
| potassium bicarbonate | 695 |
| sodium carbonate | 80 |
| Polyvinylpyrrolidone | 2 wt. % |
| Xylitol | 200 |
| polyethylene glycol 8000 | 45 |
| Flavorant | 50 |
| Colorant | 5 |

In a first mixer, etidronate, lansoprazole, part of the sodium bicarbonate, part of the potassium bicarbonate, polyethylene glycol, and polyvinylpyrrolidone are blended and then the mixture is roller compacted. In a second mixer, citric acid, sodium citrate monobasic, potassium sodium tartrate, the remaining sodium bicarbonate and potassium bicarbonate, sodium carbonate, colorant, flavorant, and xylitol are blended and then roller compacted. The mixtures from the first and second mixer are then granulated through a suitable screen. The remaining ingredients are added and the mixture is blended until uniform.

The tablet mixture is compressed on a suitable commercially available rotary tablet press. The process is carried out at room temperature and with a relative humidity not higher than 15-20%. The dies are lined with nylon inserts and/or lubricated with a thin film of paraffin oil or magnesium stearate, which is applied by spraying. The tablets are filled on-line into tubes or strips.

The tablet when dissolved in 120 ml water produces a solution having a buttered pH of about 4.0 to about 4.4.

EXAMPLE 6

This example demonstrates that the bioavailability of etidronate from effervescent tablets is greater than that obtained with non-effervescent etidronate tablets.

A group of 6 beagle dogs is dosed with etidronate following a random three-way design with a two-week washout between each treatment phase. In the first treatment phase (control), the beagle dogs are administered Didronel® (etidronate) tablets (200 mg). In the second and third treatment phases, the beagle dogs are administered effervescent tablets of the invention containing 200 mg etidronate active ingredient in either a buffered or unbuffered formulation, respectively.

For each treatment phase, the bioavailability of etidronate in the beagle dogs is determined. Urine samples are collected after 24 and 48 hours and the concentration of etidronate for each sample is determined by chromatographic analysis. The amount of etidronate found in the urine reflects the percentage of etidronate that was absorbed by the body but did not bind to the surface of the bone. While the amount of etidronate absorbed by the body is dependent on the mode of administration, the percentage of the absorbed etidronate that becomes bound to the bone surface is independent of the mode of drug administration. Thus, an increase in the amount of etidronate in the urine is reflective of an overall increase in absorption.

For the first treatment phase group of beagle dogs (control), the amount of etidronate absorbed into the body is expected to be about 3%. For the second and third treatment phase group (invention), the amount of etidronate absorbed into the body is expected to be about 6% to about 10%. Thus, the bioavailability of etidronate in treatment phase groups 2 and 3 is expected to at least 50% greater than the bioavailability from conventional tablet formulations administered to treatment phase group 1.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following clams) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best made known to the inventors for carrying out the invention. Of course, variations of those preferred embodiments will become apparent to those of ordinary skill in the an upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An effervescent composition comprising:
   (a) 50 mg to 120 mg of a bisphosphonate
   (b) citric acid, and
   (c) an alkaline effervescing component which is a carbonate salt or a bicarbonate salt, wherein the composition has a total weight of 3500 mg to about 6000 mg and when dissolved in water produces a solution having a buffered pH of about 4 to about 6.5 and has buffering capacity sufficient to mediate the pH of a patient's stomach for at least 15 minutes.

2. The composition of claim 1, wherein the bisphosphonate is selected from the group consisting of etidronate, risedronate, ibandronate, alendronate, and combinations thereof.

3. The composition of claim 1, wherein the bisphosphonate is alendronate and said buffering capacity sufficient to mediate the pH of a patient's stomach for at least 30 minutes.

4. The composition of claim 1, wherein the dissolved buffered solution is capable of mediating the pH of a patient's stomach for at least about 30 minutes or more.

5. The composition of claim 1, wherein the alkaline effervescing component comprises a carbonate salt and a bicarbonate salt.

6. The composition of claim 1, wherein the acid component and the alkaline effervescing component are at least partially reacted with each other during granulation with the bisphosphonate.

* * * * *